(12) United States Patent
Folger et al.

(10) Patent No.: US 11,446,107 B2
(45) Date of Patent: Sep. 20, 2022

(54) SPINAL IMPLANT PACKAGING

(71) Applicant: Warsaw Orthopedic, Inc., Warsaw, IN (US)

(72) Inventors: Leigh Anna Folger, Memphis, TN (US); David Mire, Collierville, TN (US); Caleb D. Smith, Collierville, TN (US); Christine Carmer, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 363 days.

(21) Appl. No.: 16/225,935

(22) Filed: Dec. 19, 2018

(65) Prior Publication Data

US 2020/0197120 A1 Jun. 25, 2020

(51) Int. Cl.
*A61B 50/30* (2016.01)
*A61B 17/70* (2006.01)
*A61B 17/86* (2006.01)
*A61B 50/00* (2016.01)

(52) U.S. Cl.
CPC .......... *A61B 50/30* (2016.02); *A61B 17/7001* (2013.01); *A61B 2050/0056* (2016.02)

(58) Field of Classification Search
CPC ............ A61B 50/30; A61B 2050/0056; A61B 2050/0051; A61B 50/3001; A61B 2020/0052; A61B 2050/3013
See application file for complete search history.

(56) References Cited

U.S. PATENT DOCUMENTS

| | | | |
|---|---|---|---|
| 4,061,226 A * | 12/1977 | Essen | B65D 85/38 206/306 |
| 4,623,336 A | 11/1986 | Pedicano et al. | |
| 4,923,059 A | 5/1990 | Evers et al. | |
| 5,036,889 A | 8/1991 | Pherigo | |
| 7,451,870 B2 * | 11/2008 | Donahoe | A61B 50/30 220/826 |
| 2007/0295620 A1 * | 12/2007 | Collet | A61C 8/0087 206/63.5 |
| 2013/0161344 A1 | 6/2013 | Park et al. | |
| 2016/0074118 A1 * | 3/2016 | Tuechsen | A61B 17/865 206/572 |
| 2017/0095308 A1 * | 4/2017 | Roesler | B65D 81/05 |
| 2020/0155207 A1 * | 5/2020 | D'Andrea | A61B 17/8872 |

* cited by examiner

*Primary Examiner* — Kevin T Truong
*Assistant Examiner* — Tracy L Kamikawa
(74) *Attorney, Agent, or Firm* — Sorell, Lenna & Schmidt, LLP

(57) ABSTRACT

A spinal implant package includes a sleeve defining a cavity extending through an end surface of the sleeve. A cap defines an aperture extending through an end surface of the cap. First portions of the end surfaces are joined to define a hinge. The end surface of the sleeve includes a second portion defining a first lip. The end surface of the cap includes a second portion defining a second lip. The package is movable between a closed configuration in which the first lip is adjacent the second lip and a portion of the spinal implant is enclosed within the cavity and the aperture, and an open configuration in which the first lip is spaced farther apart from the second lip and the portion of the spinal implant is positioned outside of the aperture while remaining positioned inside of the cavity.

20 Claims, 4 Drawing Sheets

SPINAL IMPLANT PACKAGING

TECHNICAL FIELD

The present disclosure generally relates to medical devices for the treatment of musculoskeletal disorders, and more particularly to spinal implant packaging.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Set screws may be used to fix the rods to the fasteners. Surgical treatment may employ surgical instruments and implants that are manipulated for engagement with vertebrae to position and align one or more vertebrae.

Implants, such as, for example, the fasteners, rods and set screws are typically delivered to medical personnel in molded packages. However, such packages typically require that the implants be touched by medical personnel to remove the implants from the package, thus compromising the sterility of the implants. Furthermore, such packages are often bulky and therefore result in a significant amount of medical waste. This disclosure describes an improvement over these prior technologies.

SUMMARY

In one embodiment, in accordance with the principles of the present disclosure, a spinal implant package includes a sleeve defining a cavity extending through an end surface of the sleeve. A cap defines an aperture extending through an end surface of the cap. First portions of the end surfaces are joined to define a hinge. The end surface of the sleeve includes a second portion defining a first lip. The end surface of the cap includes a second portion defining a second lip. The package is movable between a closed configuration in which the first lip is adjacent the second lip and a portion of the spinal implant is enclosed within the cavity and the aperture, and an open configuration in which the first lip is spaced farther apart from the second lip and the portion of the spinal implant is positioned outside of the aperture while remaining positioned inside of the cavity.

In one embodiment, in accordance with the principles of the present disclosure, a surgical system includes a bone fastener comprising a screw and a head coupled to the screw. The surgical system includes a package comprising a sleeve defining a cavity extending through an end surface of the sleeve. A cap defines an aperture extending through an end surface of the cap. First portions of the end surfaces are joined to define a hinge. The end surface of the sleeve includes a second portion defining a first lip. The end surface of the cap includes a second portion defining a second lip. The package is movable between a closed configuration in which the first lip is adjacent the second lip and the head is enclosed within the cavity and the aperture, and an open configuration in which the first lip is spaced farther apart from the second lip and the head is positioned outside of the aperture.

In one embodiment, in accordance with the principles of the present disclosure, a method of removing a bone fastener from a package includes: providing the bone fastener, the bone fastener comprising a screw and head coupled to the screw; providing the package, the package comprising a sleeve defining a cavity extending through an end surface of the body, the package comprising a cap defining an aperture extending through an end surface of the cap, wherein first portions of the end surfaces are joined to define a hinge, the end surface of the sleeve including a second portion defining a first lip, the end surface of the cap including a second portion defining a second lip, the screw being positioned in the cavity, the head being positioned in the cavity and the aperture; rotating the cap relative to the sleeve to move the package from a closed configuration in which the first lip is adjacent the second lip and the head is enclosed within the cavity and the aperture, to an open configuration in which the first lip is spaced farther from the second lip and the head is positioned outside of the aperture; and removing the bone fastener from the package.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
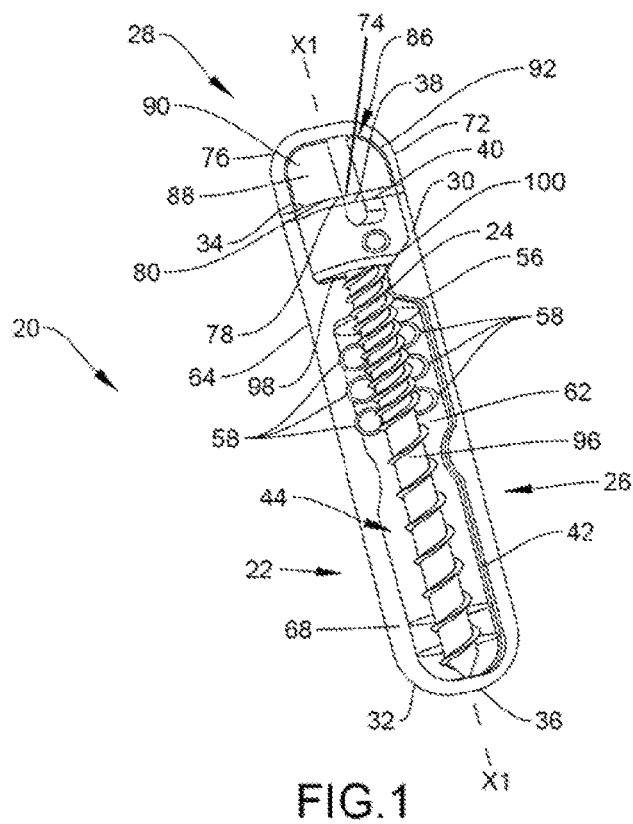
FIG. 1 is a first perspective view of one embodiment of a package and a spinal implant of a surgical system, in accordance with principles of the present disclosure.

The exemplary embodiments of the surgical system and related methods of use disclosed are discussed in terms of medical devices for the treatment of musculoskeletal disorders and more particularly, in terms of a surgical system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, one or all of the components of the surgical system may include disposable, peel-pack, pre-packed sterile devices. In some embodiments, the components of the surgical system are configured for one-time use and are disposed after they are used one time. However, it is contemplated that one or all of the components of the surgical system may be reusable. The surgical system may be configured as a kit with multiple sized and configured components, including, for example, various bone fasteners. In some embodiments, one or more of the components of the surgical system are configured to be sterilized.

In some embodiments, the disclosed packages, implants, surgical methods and systems may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The packages, implants, methods and systems of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context dearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior."

Further, as used in the specification and including the appended claims, "treating" or "treatment" of a disease or condition refers to performing a procedure to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there are illustrated components of a surgical system 20 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Figure 2:
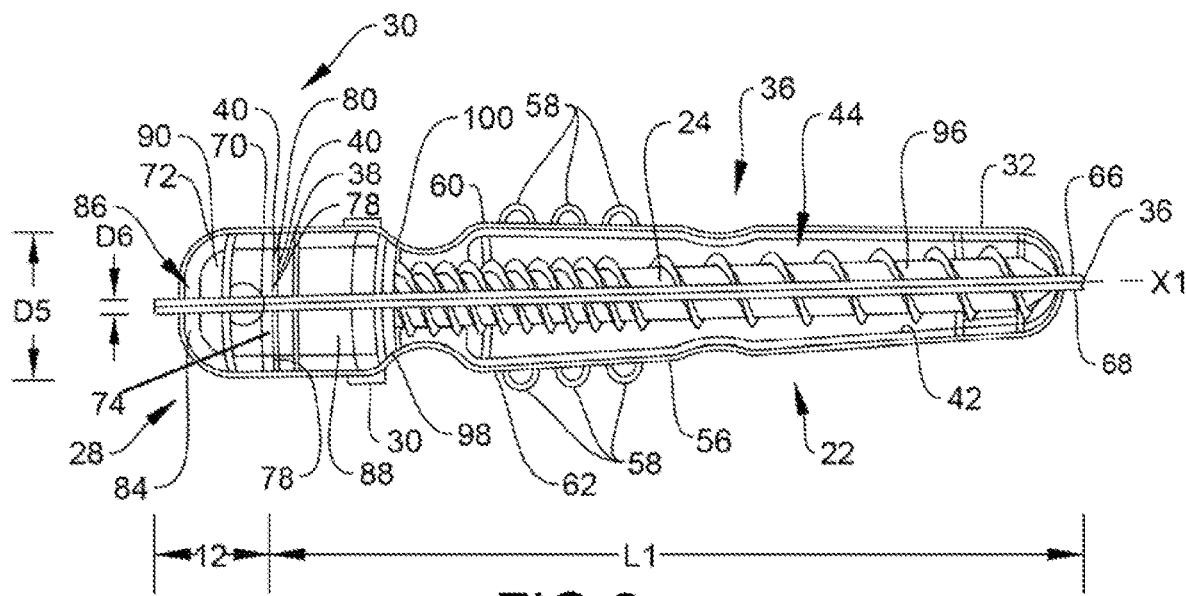
FIG. 2 is a side view of the surgical system shown in FIG. 1.
Figure 3:
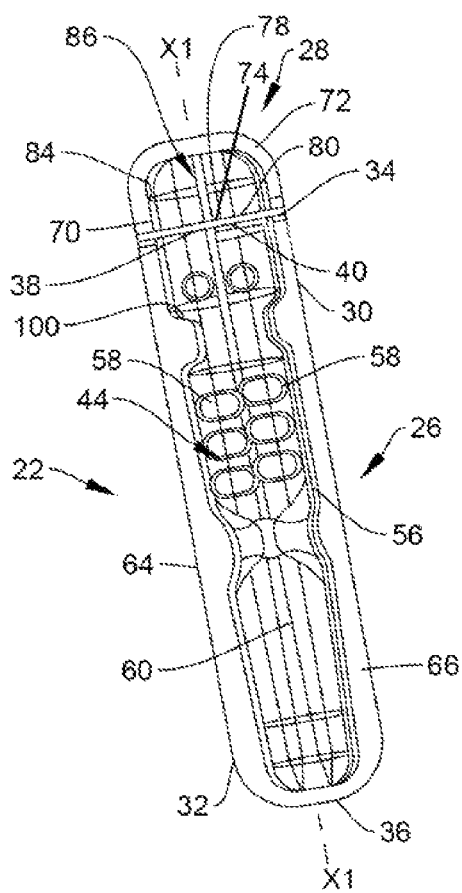
FIG. 3 is a first perspective view of the package shown in FIG. 1.
Figure 4:
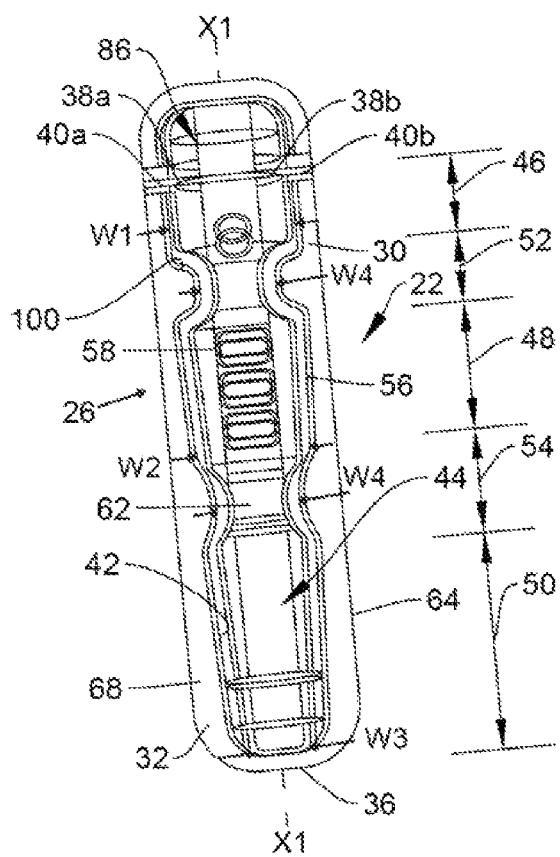
FIG. 4 is a second perspective view of the package shown in FIG. 1.

Surgical system 20 includes a package 22 and a spinal implant configured for disposal in package 22, such as, for example, spinal implant 24. However, it is envisioned that surgical system 20 may include one or a plurality of spinal implants other than spinal implant 24, as discussed herein. Package 22 includes a sleeve 26 and a cap 28 that is coupled to sleeve 26. Sleeve 26 extends along a longitudinal axis X1 between an end 30 and an opposite end 32. End 30 includes an end surface 34 and end 32 includes an end surface 36 opposite end surface 34. Sleeve 26 has a length L1 defined by the distance from end surface 34 to end surface 36, as shown in FIG. 2. End surface 34 includes a first portion 38 and a second portion 40 defining a lip, as discussed herein. Portion 40 includes a first end 40a that extends from a first end 38a of portion 38 and a second end 40b that extends from a second end 38b of portion 38, as best shown in FIG. 4, such that portion 40 is positioned between ends 38a, 38b. Portion 38 is coupled to cap 28 to join cap 28 with sleeve 26, as discussed herein. In some embodiments, portion 38 is positioned between ends of portion 40, as best shown in FIG. 4.

In some embodiments, package 22 is monolithic. For example, in some embodiments, cap 28 is integrally and/or monolithically formed with sleeve 26. In some embodiments, package 22 comprises a flexible material to facilitate removing implant 24 from package 22, as discussed herein. In some embodiments, package 22 comprises a flexible material to facilitate removing implant 24 from package 22, as discussed herein. In some embodiments, package 22 is translucent or transparent to facilitate viewing of implant 24 within package 22, as discussed herein.

Figure 5:
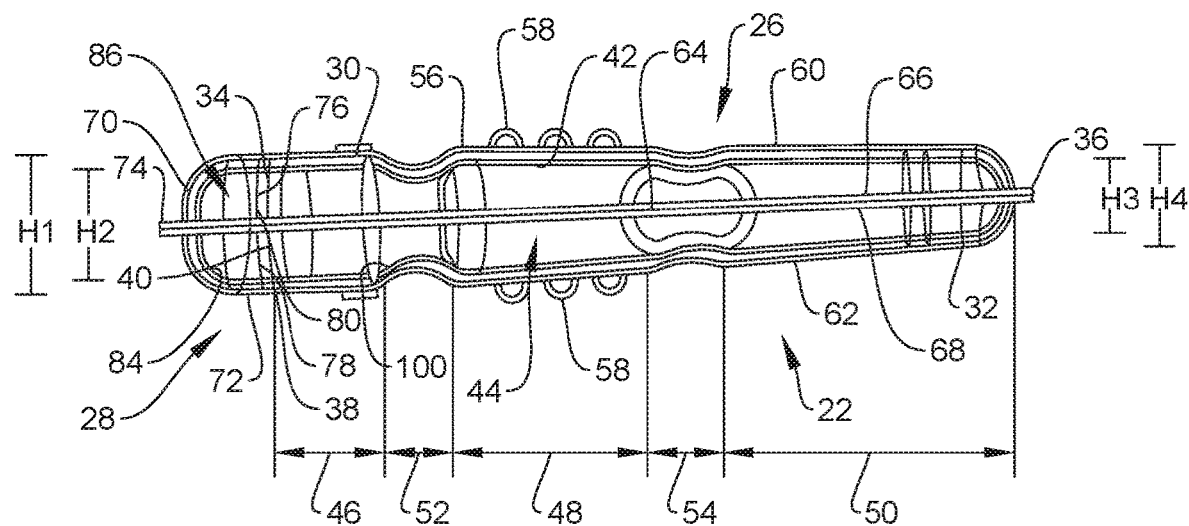
FIG. 5 is a side view of the package shown in FIG. 1.
Figure 6:
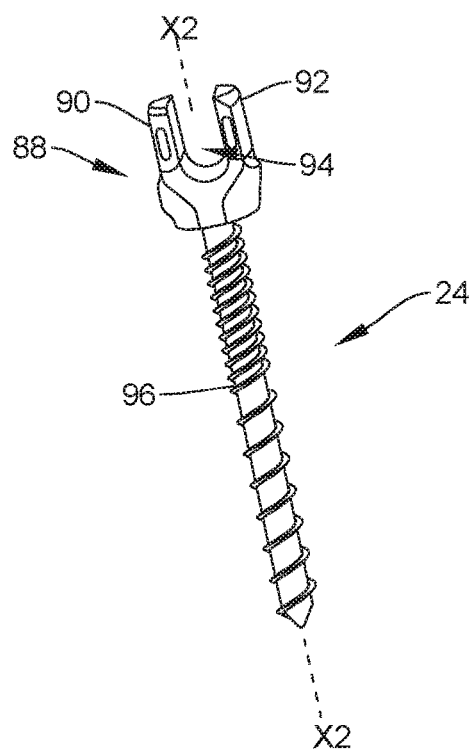
FIG. 6 is a perspective view of the spinal implant shown in FIG. 1.

Sleeve 26 includes an inner surface 42 defining a cavity 44. Cavity 44 includes a first section 46, a second section 48 and a third section 50, as best shown in FIGS. 4 and 5. Section 48 is spaced apart from section 46 by a fourth section 52 and section 50 is spaced apart from section 48 by a fifth section 54. In various embodiments, section 46 has a minimum width W1 that is greater than a minimum width W2 of section 48, as shown in FIG. 4. In various embodiments, section 50 has a minimum width W3 that is less than minimum width W2 of section 48. One or both of sections 52, 54 can have a minimum width W4 that is greater than minimum width W3 of section 50. In various embodiments, the minimum widths of sections 52 and 54 are not the exact same. In some embodiments, minimum width W4 of sections 52, 54 is equal to minimum width W2 of section 48. In some embodiments, minimum width W4 of sections 52, 54 is less than minimum width W2 of section 48. In some embodiments, minimum width W4 of sections 52, 54 is greater than minimum width W2 of section 48. In some embodiments, the width of section 48 is tapered from a maximum width at or adjacent where it meets section 52 to the minimum width W2 at or adjacent where it meets section 54, and the width of section 50 is tapered from a maximum width at or adjacent where it meets section 54 to the minimum width W3 at or adjacent where it meets end 32. In some embodiments, the width of section 48 is continuously tapered from section 52 to section 54 and the width of section 50 is continuously tapered from section 54 to end 32.

In various embodiments, section 46 has a minimum height H1 that is greater than a minimum height H2 of section 48, as shown in FIG. 5. In contemplated embodiments, H2 is the same as or greater than H1. Section 50 has a minimum height H3 that is less than minimum height H2 of section 48. In various embodiments, sections 52, 54 each have a minimum height H4 that is greater than minimum height H3 of section 50. In various embodiments, the minimum heights of sections 52 and 54 are not the exact same. In some embodiments, minimum height H4 is equal to minimum height H2 of section 48. In some embodiments, minimum height H4 is less than minimum height H2 of section 48. In some embodiments, minimum height H4 is greater than minimum height H2 of section 48. In some embodiments, the height of section 48 is tapered from section 52 to section 54 and the height of section 50 is tapered from section 54 to end 32. In some embodiments, the height of section 48 is continuously tapered from section 52 to section 54 and the height of section 50 is continuously tapered from section 54 to end 32.

In some embodiments, section 46, section 48, section 50, section 52 and/or section 54 may have various cross section configurations, such as, for example, oval, oblong, triangular, rectangular, square, polygonal, irregular, uniform, non-uniform, variable, tubular and/or tapered. In some embodiments, section 46 gradually transitions into section 52. That is, cavity 44 has an arcuate configuration between section 46 and section 52 that allows for the creation of a neck between section 46 and section 52, without creating a ledge, to prevent a spinal implant from being snagged when inserted into cavity 44. Indeed, because there is no square interface between section 46 and section 52, the spinal implant can slide along the arcuate neck between section 46 and 52. In some embodiments, section 52 gradually transitions into section 48. That is, cavity 44 has an arcuate configuration between section 52 and section 48 that allows for the creation of a neck between section 52 and section 48, without creating a ledge, to prevent a spinal implant from being snagged when inserted into cavity 44. Indeed, because there is no square interface between section 52 and section 48, the spinal implant can slide along the arcuate neck between section 52 and 48. In some embodiments, section 48 gradually transitions into section 54. That is, cavity 44 has an arcuate configuration between section 48 and section 54 that allows for the creation of a neck between section 48 and section 54, without creating a ledge, to prevent a spinal implant from being snagged when inserted into cavity 44. Indeed, because there is no square interface between section 48 and section 54, the spinal implant can slide along the arcuate neck between section 48 and 54. In some embodiments, section 54 gradually transitions into section 50. That is, cavity 44 has an arcuate configuration between section 54 and section 50 that allows for the creation of a neck between section 54 and section 50, without creating a ledge, to prevent a spinal implant from being snagged when inserted into cavity 44. Indeed, because there is no square interface between section 54 and section 50, the spinal implant can slide along the arcuate neck between section 54 and 50.

Sleeve 26 includes an outer surface 56 opposite surface 42. In some embodiments, surface 56 comprises one or a plurality of protrusions, such as, for example, one or a plurality of bumps 58 to facilitate gripping of package 22, as discussed herein. In some embodiments, package 22 includes one or a plurality of bumps 58 on a first side 60 of sleeve 26 and one or a plurality of bumps 58 on an opposite second side 62 of sleeve 26, as best shown in FIGS. 2 and 5. The bumps 58 are in various embodiments positioned in section 48, as shown. In some embodiments, bumps 58 can have various shape configurations, such as, for example, oval, oblong, polygonal, irregular, uniform, non-uniform, variable and/or tapered. The distance between side 60 and side 62 defines a dimension D5 of sleeve 26, as shown in FIG. 2. Sleeve 26 includes a flange or wall 64 positioned between side 60 and side 62. In some embodiments, wall 64 extends from an area where side 60 meets side 62. Wall 64 surrounds cavity 44 and includes a planar top surface 66 and an opposite planar bottom surface 68. Wall 64 has a dimension D6 defined by the distance between surface 66 and surface 68. In various embodiments, dimension D6 is uniform along the entire length of wall 64. Dimension D5 is greater than dimension D6 along the entirety of length L.

Cap 28 extends along axis X1 between an end 70 and an opposite end 72. End 70 includes an end surface 74 and end 72 includes an end surface 76 opposite end surface 74. Cap 28 has a length L2 defined by the distance from end surface 74 to end surface 76, as shown in FIG. 2. Length L2 is less than length L1. However, it is envisioned that length L2 may be greater than or equal to length L1, depending upon the requirements of a particular application, such as, for example, the dimensions of an implant to be disposed within package 22. Length L1 and length L2 combine to define a total length of package 22. End surface 74 includes a first portion 78 and a second portion 80 defining a lip, as discussed herein. Portion 78 is coupled to portion 38 to form a hinge 82 that joins cap 28 with sleeve 26 such that cap 28 is rotatable and/or pivotable relative sleeve 26, as discussed herein. In some embodiments, portion 78 is positioned between ends of portion 80, as best shown in FIG. 4. In some embodiments, portion 78 is integrally and/or monolithically formed with portion 38 such that hinge 82 is a living hinge. In some embodiments, portion 78 and/or portion 38 are thinned or cut relative to other portions of cap 28 and/or sleeve 26 to allow bending along hinge 82. Cap 28 includes an inner surface 84 defining an aperture 86 configured for disposal of a portion of implant 24, as discussed herein. In some embodiments, aperture 86 may have various cross section configurations, such as, for example, oval, oblong, triangular, rectangular, square, polygonal, irregular, uniform, non-uniform, variable, tubular and/or tapered.

Figure 7:
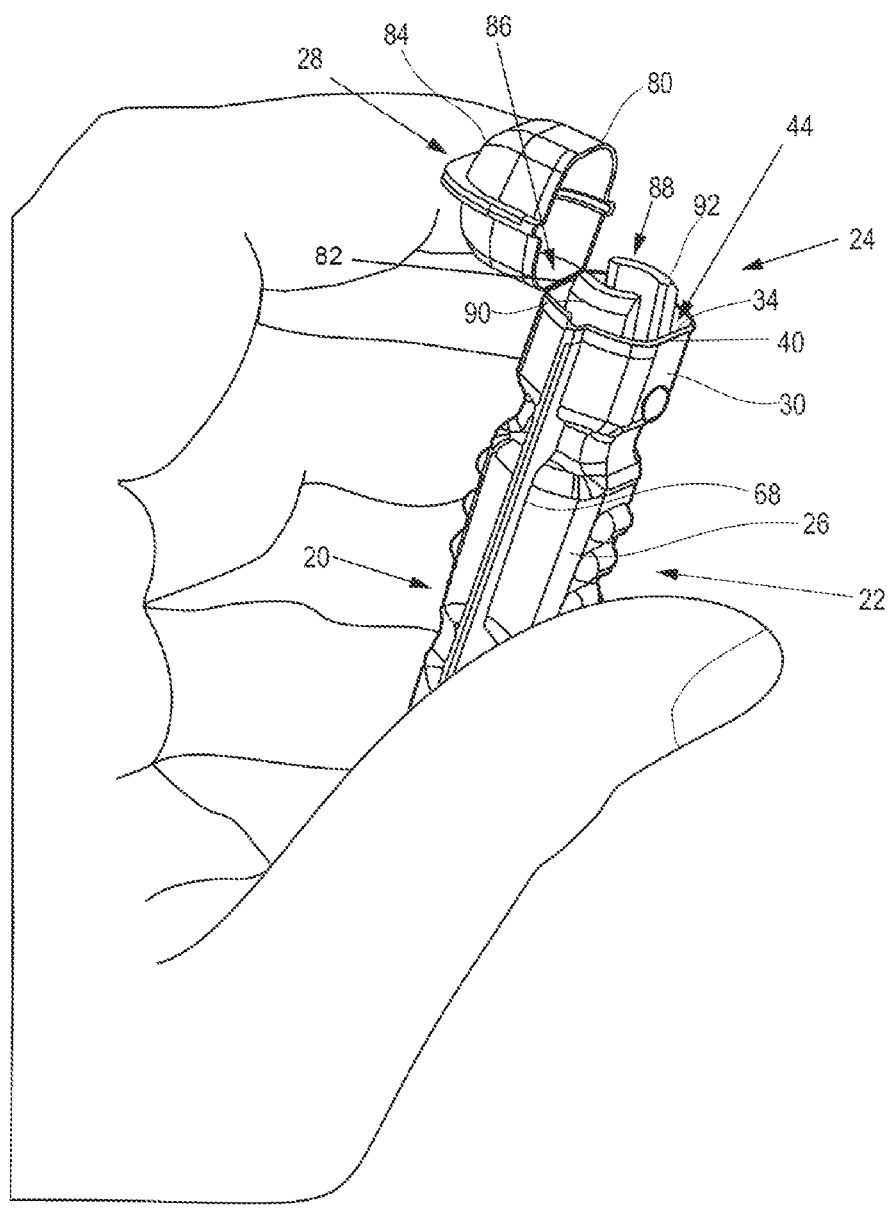
FIG. 7 is a second perspective view of the surgical system shown in FIG. 1.

Package 22 is movable between a closed configuration and an open configuration. When the package is in the closed configuration, portion 40 is adjacent portion 80, wherein the portions 40, 80 can define respective lips as mentioned. The package 22 may be configured such that, when the package is in the closed configuration, the adjacent portions 40, 80 partially or fully contact each other, or such that portion 40 is spaced a first distance apart from portion 80, as shown in FIGS. 1-5, and an open configuration in which portion 40 is spaced an increased second distance apart from portion 80, as shown in FIG. 7. Package 22 moves between the closed configuration and open configuration by rotating cap 28 relative to sleeve 26 about hinge 82. In some embodiments, package 22 is biased to the closed configuration such that package 22 will move from the open configuration to the closed configuration without applying any external force to cap 28 or sleeve 26. For example, it is envisioned that sleeve 26, cap 28 and/or hinge 82 may include one or more materials having elastic properties such that package 22 will move from the open configuration to the closed configuration when a force applied to cap 28 to move package from the closed configuration to the open configuration is removed. In some embodiments, package 22 includes one or more closure elements configured to maintain package 22 in the closed configuration unless and until a force is applied. For example, it is envisioned that sleeve 26 can include a first closure element and that cap 28 can include a second closure element configured to engage the first closure element to maintain package 22 in the closed configuration. The closure elements will maintain package 22 in the closed configuration unless and until a force is applied to separate the first closure element from the second closure element such that the first closure element is spaced apart from the second closure element. Once the first closure element is spaced apart from the second closure element, package 22 may be moved from the closed configuration to the open configuration by rotating cap 28 relative to sleeve 26 about hinge 82, as discussed herein. In some embodiments, the closure elements include, for example, mutual grooves, screws, adhesive, nails, barbs, raised elements, spikes, dips, snaps, friction fittings, compressive fittings, expanding rivets, staples, fixation plates, key/keyslot, tongue in groove, dovetail, magnetic connection and/or posts.

Implant 24 includes a head, such as, for example, a receiver 88 having a pair of spaced apart arms 90, 92. Receiver 88 is configured for disposal in section 46 of cavity 44 and aperture 88 such that a bottom surface 98 of receiver 88 directly engages a shoulder 100 of sleeve 26, as shown in FIGS. 1 and 2. Arms 90, 92 include an inner surface that defines a U-shaped passageway 94. Passageway 94 is configured for disposal of an implant, such as, for example, a spinal rod. In some embodiments, all or only a portion of passageway 94 may have alternate cross section configurations, such as, for example, oval, oblong, triangular, square, polygonal, irregular, uniform, non-uniform, offset, staggered, and/or tapered. In some embodiments, arms 90, 92 may be disposed at alternate orientations, relative to a longitudinal axis X2 of implant 24, such as, for example, transverse, perpendicular and/or other angular orientations such as acute or obtuse, co-axial and/or may be offset or staggered. The inner surface of receiver 88 includes a thread form configured for engagement with a set screw.

Implant 24 includes a screw, such as, for example, a shaft 96 configured for penetrating tissue. Shaft 96 is configured for disposal in sections 48, 50, 52, 54 of cavity 44, as shown in FIGS. 1 and 2. Shaft 96 includes a proximal portion positioned within an aperture of receiver 88 such that shaft 96 is rotatable and/or pivotable relative to receiver 88 in a plurality of axes and/or planes to define a multi-axial screw. Shaft 96 has a cylindrical cross-sectional configuration and includes an outer surface having an external thread form. In some embodiments, the external thread form may include a single thread or a plurality of discrete threads. In some embodiments, other engaging structures may be located on shaft 96, such as, for example, a nail configuration, barbs, expanding elements, raised elements and/or spikes to facilitate engagement of shaft 96 with tissue.

In some embodiments, all or only a portion of shaft 96 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 96 may include one or a plurality of openings. In some embodiments, all or only a portion of the outer surface of shaft 96 may have alternate surface configurations to enhance fixation with tissue, such as, for example, rough, arcuate, undulating, mesh, porous, semiporous, dimpled and/or textured. In some embodiments, all or only a portion of shaft 96 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 96 may be cannulated.

In assembly, operation and use, surgical system 20 is employed to treat an affected section of vertebrae. A medical practitioner obtains access to a surgical site including the vertebrae in any appropriate manner, such as through incision and retraction of tissues. The components of surgical system 20 including package 22 and a spinal implant (e.g., implant 24) are employed to augment a surgical treatment. Package 22 can be delivered to an operating room with package 22 in the closed configuration with receiver 88 disposed in section 46 of cavity 44 and aperture 88 such that bottom surface 98 directly engages shoulder 100 and shaft 96 disposed in sections 48, 50, 52, 54 of cavity 44, as discussed herein. In some embodiments, package 22 is positioned in a sterile container when package 22 is delivered to the operating room to maintain the sterility of package 22 and the spinal implant positioned within package 22. For example, the container may include a tray configured to house package 22 and a lid that attaches to the tray to cover the tray. The container may be sterilized before and/or after package 22 is positioned in the tray and the lid covers the tray. In some embodiments, the container is delivered to the operating room with the lid of the container covering the tray of the container and package 22 positioned within the tray such that package 22 and the spinal implant within package 22 are both sterile when delivered to the operating room. Surgical system 20 may be may be completely or partially revised, removed or replaced.

Surgical system 20 may be used with surgical methods or techniques including open surgery, mini-open surgery, minimally invasive surgery and percutaneous surgical implantation, whereby the vertebrae are accessed through a mini-incision, or sleeve that provides a protected passageway to the area. Once access to the surgical site is obtained, a surgical treatment, for example, corpectomy and/or discectomy, can be performed for treating a spine disorder.

Surgical system 20 can include one or a plurality of bone fasteners and/or fixation elements, such as, for example, implant 24, which may be employed with a single vertebral level or a plurality of vertebral levels. In some embodiments, the bone fasteners are each disposed within a package 22 when delivered to an operating room. In some embodiments, the bone fasteners are each sterilized before being inserted into packages 22. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

The lids of the containers are moved so as not to cover the trays of the containers. Packages 22 are removed from the trays of the containers. Packages 22 are moved from the closed configuration to the open configuration to provide a medical practitioner access to the bone fasteners. In one embodiment, a respective one of packages 22 is moved from the closed configuration to the open configuration by grasping sleeve 26 with one or more fingers and pushing cap 28 with another finger such that cap 28 rotates relative to sleeve 26 about hinge 82. This allows packages 22 to be moved between the open and closed configurations using only one hand. That is, only one hand is required to move packages 22 between the open and closed configurations. However, it is envisioned that two or more hands may be used to move packages 22 between the open and closed configurations, if desired. In some embodiments, when the packages 22 are in the open configuration, sides 60, 62 of a respective package 22 are squeezed to remove a respective one of the bone fasteners from cavity 44. For example, in one embodiment, the package 22 can be squeezed such that receiver 88 and shaft 96 move out of cavity 44 and implant 24 falls onto a surface in the operating room, such as, for example, a sterilized table or tray without the medical practitioner touching any components. This prevents contamination of the sterilized bone fastener. In some embodiments, when the packages 22 are in the open configuration, a respective package 22 is inverted to remove a respective one of the bone fasteners from cavity 44. For example, in one embodiment, the package 22 can be inverted such that receiver 88 and shaft 96 move out of cavity 44 and implant 24 falls (dumps) onto a surface in the operating room, such as, for example, a sterilized table or tray without the medical practitioner touching any components. In one embodiment, package 22 is inverted using only one hand. That is, the same hand that is used to move package between the open and closed configurations can be used to invert package 22 to dump implant 24 onto the surface in the operating room. In some embodiments, when the packages 22 are in the open configuration, the bone fasteners can be grasped with sterile forceps or a sterile tulip head inserter and removed from package 22 using the forceps or the sterile tulip head inserter. For example, in one embodiment, sterile forceps or a sterile tulip head inserter are used to engage implant 24 and lift implant 24 out of cavity 44 to remove implant 24 from package 22 without the medical practitioner touching any components. In some embodiments, packages 22 are discarded after the bone fasteners are removed from packages 22. Once removed from packages 22, the bone fasteners can be engaged with vertebrae in various orientations, such as, for example, series, parallel, offset, staggered and/or alternate vertebral levels. One or more spinal rods may be engaged with the bone fasteners. For example, in one embodiment, a spinal rod is inserted into passageways 94 of implanted implants 24. Set screws are threaded with arms 90, 92 to fix the rod relative to implants 24.

In some embodiments, a kit containing one or more components of surgical system 20 is provided. The kit may comprise components from any of the embodiments discussed herein. In some embodiments, the kit comprises one or more of packages 22. In some embodiments, the kit comprises one or more implants, such as, for example, one or more of the bone fasteners discussed herein. In some embodiments, the kit comprises one or spinal rods, such as, for example, spinal rods having different lengths, straight spinal rods, pre-bent spinal rods and/or spinal rods made from different materials. In some embodiments, the kit comprises a plurality of set screws, such as, for example, different size set screws and/or set screws made from different materials. In some embodiments, the kit comprises one or a plurality of instruments, such as, for example, forceps or tulip head inserters to remove implants from the packages. In some embodiments, the kit comprises one or a plurality of instruments to implant the implants, such as, for example, one or more rod inserters and/or drivers.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A package for a spinal implant, the package comprising:
   a sleeve having a proximal end surface and defining a cavity; and
   a cap having a distal end surface and defining an aperture, the cavity and the aperture being sized and shaped to together house the spinal implant;
   wherein a first portion of the proximal end surface and a first portion of the distal end surface are joined to define a living hinge, the proximal end surface including a second portion defining a first lip, the distal end surface including a second portion defining a second lip,
   wherein the package is movable between a closed configuration in which the first lip is adjacent the second lip for enclosing a portion of the spinal implant within the cavity and the aperture, and an open configuration in which the first lip is spaced farther apart from the second lip than any spacing between the first lip and the second lip in the closed configuration so that the spinal implant would be positioned outside of the aperture while remaining positioned inside of the cavity, wherein the cavity comprises a first section, a second section, a third section, a fourth section and a fifth section, the second section being positioned between the first section and the third section, the fourth section being positioned between the third section and the fifth section, the first section and the third section each having a minimum width greater than a minimum width of the second section and a minimum width of the fourth section, the first section extending through the proximal end surface, and the fifth section separated from the proximal end surface by the other sections of the cavity, wherein the cap is positioned proximal to the sleeve when the package is in the closed configuration such that the cap is coaxial with the sleeve to entirely cover the first section of the cavity, wherein the package is free of any obstructions between the cavity and the aperture when the package is in the closed configuration such that the first section of the cavity opens into the aperture, and wherein the sleeve is formed by a wall with an inner surface that defines the sections of the cavity and with an opposite outer surface that defines an outer surface of the package.

2. The package as recited in claim 1, wherein:

the first lip is spaced a first distance apart from the second lip when the package is in the closed configuration, and the first lip is spaced a second distance apart from the second lip when the package is in the open configuration; and the first distance is less than the second distance.

3. The package as recited in claim 1, wherein the package is movable between the open configuration and the closed configuration using only one hand.

4. The package as recited in claim 1, wherein the outer surface of the package comprises a plurality of spaced apart bumps.

5. The package as recited in claim 1, wherein the minimum width of the second section is not the exact same as the minimum width of the fourth section.

6. The package as recited in claim 1, wherein the minimum width of the third section is less than the minimum width of the first section.

7. The package as recited in claim 6, wherein a minimum width of the fifth section is less than the minimum width of the first section.

8. The package as recited in claim 1, wherein the package comprises a material that is flexible and/or translucent.

9. The package as recited in claim 1, wherein the package is monolithic.

10. The package as recited in claim 1, wherein the cap is monolithic.

11. The package as recited in claim 1, wherein the package includes only one hinge connecting the cap to the sleeve.

12. The package as recited in claim 1, wherein the package includes a flange, the flange including a planar top surface and an opposite planar bottom surface.

13. The package as recited in claim 1, wherein the cap includes a body comprising opposite inner and outer surfaces, the inner surface defining a recess in communication with the aperture, the cap comprising a flange extending outwardly from the outer surface of the body of the cap.

14. The package as recited in claim 1, wherein the sleeve comprises a first flange surrounding three sides of the cavity and the cap comprises a second flange surrounding three sides of the aperture, the first flange having opposite top and bottom surfaces that define a dimension of the first flange, the dimension of the first flange being less than a dimension of the cavity, the second flange having opposite top and bottom surfaces that define a dimension of the second flange, the dimension of the second flange being less than a dimension of the aperture.

15. The package as recited in claim 14, wherein the top and bottom surfaces of the first flange and the top and bottom surfaces of the second flange are each planar.

16. The package as recited in claim 14, wherein the flanges define an oblong configuration of the package when the package is in the closed configuration.

17. A package for a spinal implant, the package comprising:

a sleeve having a proximal end surface and defining a cavity; and a monolithic cap having a distal end surface and defining an aperture, the cavity and the aperture being sized and shaped to together house the spinal implant;

wherein a first portion of the proximal end surface and a first portion of the distal end surface are joined to define a living hinge, the proximal end surface including a second portion defining a first lip, the distal end surface including a second portion defining a second lip, wherein the package is movable between a closed configuration in which the first lip is adjacent the second lip for enclosing a portion of the spinal implant within the cavity and the aperture, and an open configuration in which the first lip is spaced farther apart from the second lip than any spacing between the first lip and the second lip in the closed configuration so that the spinal implant would be positioned outside of the aperture while remaining positioned inside of the cavity, wherein the cavity comprises a first section, a second section, a third section, a fourth section and a fifth section, the second section being positioned between the first section and the third section, the fourth section being positioned between the third section and the fifth section, the first section and the third section each having a minimum width greater than a minimum width of the second section and a minimum width of the fourth section, the first section extending through the proximal end surface, and the fifth section separated from the proximal end surface by the other sections of the cavity, wherein the package is free of any obstructions between the cavity and the aperture when the package is in the closed configuration such that the first section of the cavity opens into the aperture, wherein the cap is positioned proximal to the sleeve when the package is in the closed configuration such that the cap is coaxial with the sleeve to entirely cover the first section of the cavity, wherein the package includes only one hinge connecting the cap to the sleeve, and wherein the sleeve is formed by a wall with an inner surface that defines the sections of the cavity and with an opposite outer surface that defines an outer surface of the package.

18. The package as recited in claim 17, wherein:
the first lip is spaced a first distance apart from the second lip when the package is in the closed configuration, and the first lip is spaced a second distance apart from the second lip when the package is in the open configuration; and
the first distance is less than the second distance.

19. A package for a spinal implant, the package consisting of:
- a sleeve having a proximal end surface and defining a cavity; and
- a monolithic cap having a distal end surface and defining an aperture, the cavity and the aperture being sized and shaped to together house the spinal implant;
- wherein a first portion of the proximal end surface and a first portion of the distal end surface are joined to define a living hinge, the proximal end surface including a second portion defining a first lip, the distal end surface including a second portion defining a second lip,
- wherein the package is movable between a closed configuration in which the first lip is adjacent the second lip for enclosing a portion of the spinal implant within the cavity and the aperture, and an open configuration in which the first lip is spaced farther apart from the second lip than any spacing between the first lip and the second lip in the closed configuration so that the spinal implant would be positioned outside of the aperture while remaining positioned inside of the cavity,
- wherein the cavity comprises a first section, a second section, a third section, a fourth section and a fifth section, the second section being positioned between the first section and the third section, the fourth section being positioned between the third section and the fifth section, the first section and the third section each having a minimum width greater than a minimum width of the second section and a minimum width of the fourth section, the first section extending through the proximal end surface, and the fifth section separated from the proximal end surface by the other sections of the cavity,
- wherein the package is free of any obstructions between the cavity and the aperture when the package is in the closed configuration such that the first section of the cavity opens into the aperture,
- wherein the cap is positioned proximal to the sleeve when the package is in the closed configuration such that the cap is coaxial with the sleeve to entirely cover the first section of the cavity,
- wherein the package includes only one hinge connecting the cap to the sleeve, and
- wherein the sleeve is formed by a wall with an inner surface that defines the sections of the cavity and with an opposite outer surface that defines an outer surface of the package.

20. The package as recited in claim 19, wherein:
the first lip is spaced a first distance apart from the second lip when the package is in the closed configuration, and the first lip is spaced a second distance apart from the second lip when the package is in the open configuration; and
the first distance is less than the second distance.

* * * * *